United States Patent [19]
Cook

[11] Patent Number: 6,119,038
[45] Date of Patent: Sep. 12, 2000

[54] HANDHELD SKIN TREATMENT SYSTEM AND METHOD

[75] Inventor: Stuart Alan Cook, Duluth, Ga.

[73] Assignee: ProVenture, LLC, Duluth, Ga.

[21] Appl. No.: 09/196,528

[22] Filed: Nov. 20, 1998

[51] Int. Cl.⁷ .................................................. A61N 1/32
[52] U.S. Cl. ........................... 607/3; 607/150; 607/153; 604/20
[58] Field of Search ................................... 607/150, 153, 607/115, 3, 151, 50; 604/20, 19

[56] References Cited

U.S. PATENT DOCUMENTS

| | | | |
|---|---|---|---|
| 4,153,726 | 5/1979 | Borggrefe et al. | 424/313 |
| 4,323,073 | 4/1982 | Ferris . | |
| 4,590,069 | 5/1986 | Deckner et al. | 424/70 |
| 4,760,096 | 7/1988 | Sakai et al. | 514/847 |
| 4,847,083 | 7/1989 | Clark | 424/642 |
| 4,975,218 | 12/1990 | Rosser | 252/117 |
| 5,069,211 | 12/1991 | Bartelt et al. . | |
| 5,251,637 | 10/1993 | Shalvi . | |
| 5,514,167 | 5/1996 | Smith et al. . | |
| 5,931,859 | 8/1999 | Burke | 607/66 |
| 5,995,869 | 11/1999 | Cormier et al. | 607/152 |
| 6,007,502 | 12/1999 | Lee | 607/150 |

FOREIGN PATENT DOCUMENTS

WO 90/04997  11/1989  WIPO .

*Primary Examiner*—Kennedy Schaetzle
*Attorney, Agent, or Firm*—Oppenheimer Wolff & Donnelly LLP

[57] ABSTRACT

An exemplary system in accordance with the current invention includes (1) a handholdable or handheld electric skin treatment unit, (2) a recharger assembly including a low voltage power supply and a recharger mount for holding the unit, with an alphanumeric display on said unit being exposed, and mating contacts on said mount and said unit, and (3) a stand for mounting said unit in a convenient location when it is not in use. The handheld electric skin treatment unit including a housing having an internal chamber containing electrical circuitry including a microprocessor and a rechargeable battery, an alphanumeric display coupled to said microprocessor, and first and second external broad area conductive electrodes connected to said circuitry, said first conductive electrode, the palm electrode adapted to be in continuous contact with the user's hand, and said second skin electrode being adapted to apply electrical current to the skin of the user to be treated; said unit also including exposed recharging terminals for recharging said battery.

17 Claims, 11 Drawing Sheets

HANDHELD SKIN TREATMENT SYSTEM AND METHOD

FIELD OF THE INVENTION

This invention relates to an electrical skin treatment system, or device, and to a related method.

BACKGROUND OF THE INVENTION

Various arrangements have been proposed heretofore for treating the skin on the human body with low level electricity. In this regard, attention is directed to U.S. Pat. No. 5,514,167. While structurally somewhat similar, the device disclosed in that patent has no variable alphanumeric display with printed legends, is not rechargeable, and includes limited, special purpose electrical circuitry. Attention is also directed to U.S. Pat. No. 5,251,637 which is disclosed as an electrical acupuncture device with audio locating arrangements.

SUMMARY OF THE INVENTION

In accordance with a specific illustrative system aspect of the invention, it involves a system including (1) a handholdable or handheld electric skin treatment unit, (2) a recharger assembly including a low voltage power supply and a recharger mount for holding the unit, with an alphanumeric display on said unit being exposed, and mating contacts on said mount and said unit, and (3) a stand for mounting said unit in a convenient location when it is not in use. The handheld electric skin treatment unit including a housing having an internal chamber containing electrical circuitry including a microprocessor and a rechargeable battery, an alphanumeric display coupled to said microprocessor, and first and second external broad area conductive electrodes connected to said circuitry, said first conductive electrode, the palm electrode adapted to be in continuous contact with the user's hand, and said second skin electrode being adapted to apply electrical current to the skin of the user to be treated; said unit also including exposed recharging terminals for recharging said battery. The following method is employed, with appropriate steps involving the handheld unit being prompted by a read only memory associated with the microprocessor and the alphanumeric display: (1) on clean, makeup-free skin, apply alkaline pH cleanser; (2) hold skin electrode to the cheek to sense resistance and automatically set optimum current level to be used; (3) move skin electrode over all areas of the skin to be treated using negative to positive current flow; (4) wash the skin area being treated; (5) apply acidic pH moisturizer to the skin; (6) move skin electrode over all areas of the skin to be treated, using positive to negative current flow.

In accordance with a broader aspect of the invention, the method as set forth hereinabove may be accomplished with other electrical treatment units, and with a standardized current flow or an automatically adjustable current flow arrangement so that the separate sensing step, while preferred, is not necessarily included.

In accordance with another system aspect of the invention, the system may include (1) an electrical skin treatment unit with a visible state display; (2) recharger assembly including a low voltage power supply and a recharger mount for holding the skin treatment unit in position for recharging with the display exposed; and (3) a stand for mounting said skin treatment unit in a convenient location when it is charged but not in use.

In accordance with a further aspect of the invention, a handheld unit for skin treatment includes a visible alphanumeric display, a first palm or hand engaging electrode and a second skin treatment electrode, a rechargeable battery, and electrical circuitry including a microprocessor coupled to said electrodes and said display device for applying low levels of electricity to said electrodes for skin treatment, while disclosing the state of said unit on said alphanumeric display.

The skin treatment unit may also include circuitry for testing the resistance or moisture of the skin of the user, and automatically setting the power level to the optimum value corresponding to the detected resistance.

Other objects, features and advantages will become apparent from a consideration of the following detailed description, in combination with the accompanying drawings.

DETAILED DESCRIPTION OF THE PREFERRED EMBODIMENTS

Figure 1:
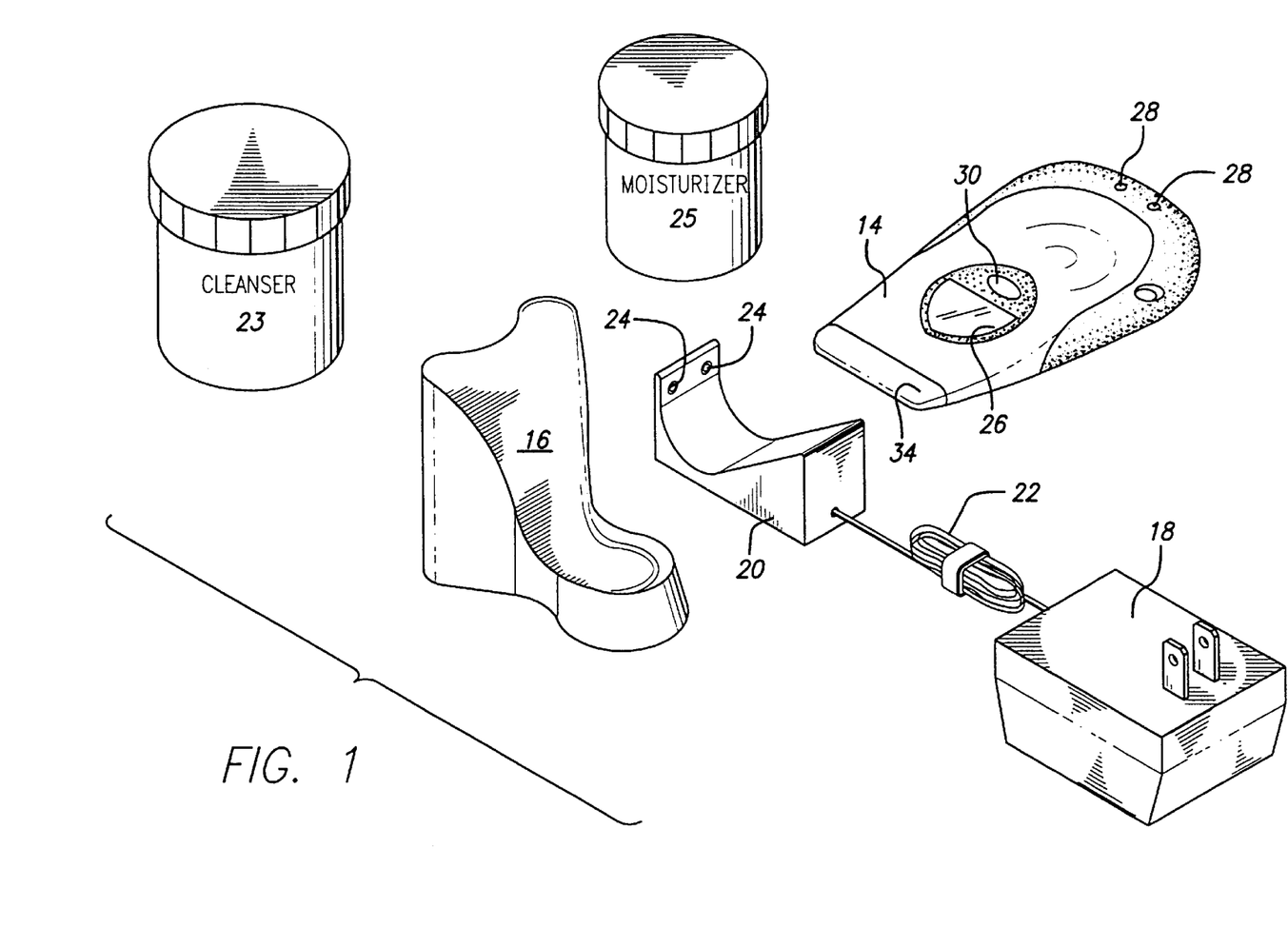
FIG. 1 is a perspective view of all of the components which go into a skin treatment system illustrating one embodiment of the invention.

Referring more particularly to the drawings, FIG. 1 shows a handheld skin treatment unit 14, a stand 16, and a recharger assembly, including a low voltage power supply 18 connected to a recharger mount 20 by wires 22. Also shown in FIG. 1 are two jars and of cleanser 23 and moisturizer 35 cream, which are used in the preferred skin treatment program or regimen, as discussed hereinbelow.

Figures 2, 3:
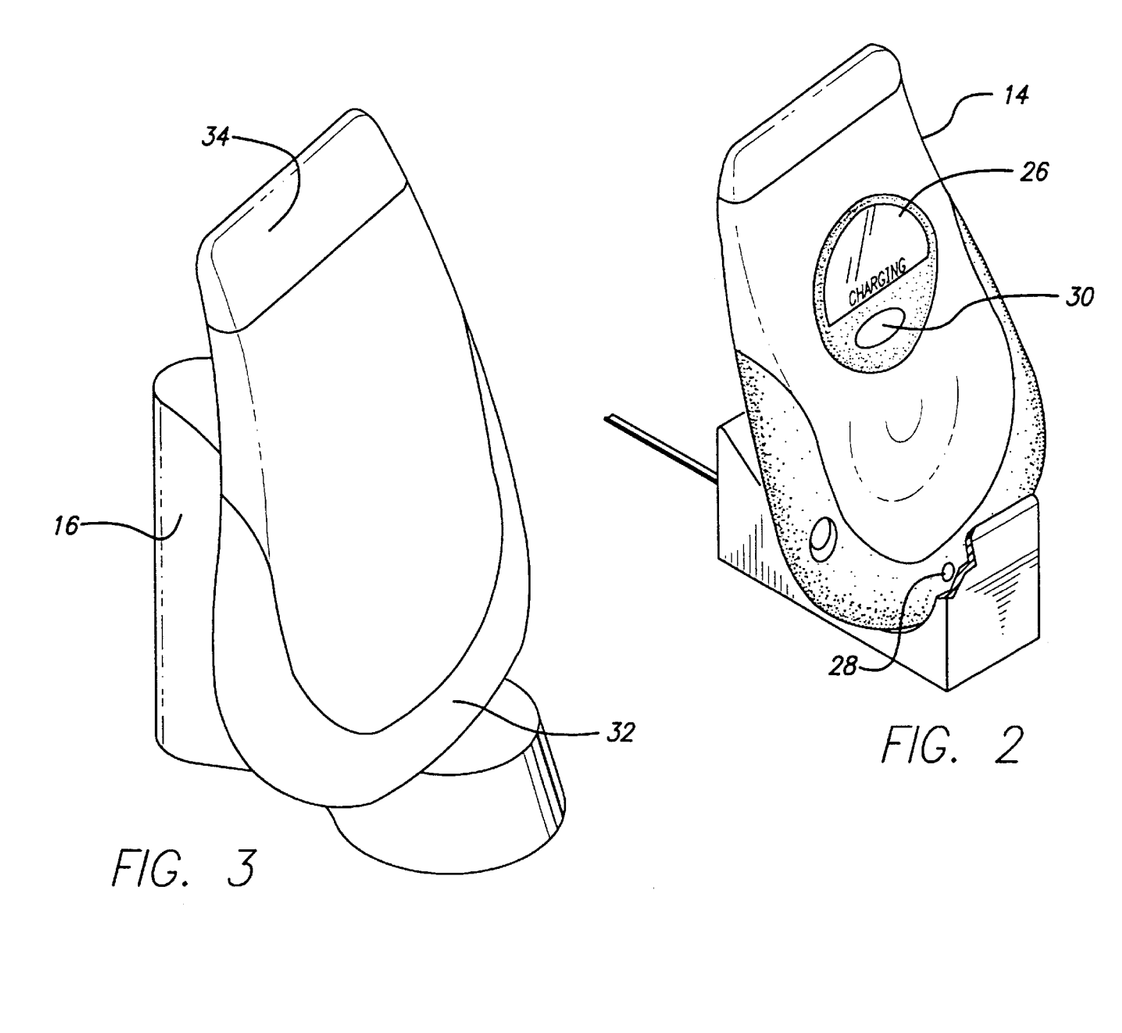
FIG. 2 shows an illustrative skin treatment unit mounted in charging position on a recharger mount.
FIG. 3 shows the skin treatment unit on a stand, with the unit available for convenient use.

As shown in FIG. 2, when the rechargeable batteries 46 for the skin treatment unit 14 are low, the treatment unit 14 is placed on the recharging mount 20 with the power supply 18 plugged into a normal 115-volt alternating current supply. When the treatment unit 14 is properly mounted into the recharger mount 20, power is supplied to the unit, and the batteries are recharged. Preferably, the treatment unit's 14 mating electrical contacts 28 engages the recharger mount's 20 mating electrical contacts 24. However, the contacts on the treatment unit 14 may be the retaining terminal screws 38 for holding the two principal portions forming the sealed housing for the unit together. Alternatively, separate mating terminals may be employed or juxtaposed coils in the mount 20 and the skin treatment unit 14 may be used to transfer charging power to the unit 14. In view of the relatively low power consumption of the skin treatment unit 14, it is contemplated that the unit 14 will not have to be recharged very frequently; and accordingly, the recharger assembly 18, 20, 22 may be stored away during intervals when recharging is not needed. Incidentally, the alphanumeric display 26, which may be a liquid crystal display (LCD), is visible when the skin treatment unit 14 is properly positioned on the mount 20. Appearing on the display 26 will be a blinking legend "LOW BATTERY" when recharging is needed. During charging, a blinking legend "CHARGING" will appear, and following full recharging, a blinking legend "DONE CHARGING" will be displayed.

FIG. 3 shows the skin treatment unit 14 on the stand 16 which may be located, for example, on the counter in a bathroom. In FIG. 3, the two electrodes employed in the actual skin treatment process are shown. The larger curved hand or palm engaging electrode 32 is located at the larger rounded end of the skin treatment unit 14, and the smaller relatively straight skin treatment electrode 34 is located at the other end of the treatment unit 14. In the course of actual electrical skin treatment, the electrical circuit extends from the treatment unit 14 through the skin treatment electrode 34 (which is moved over the face or other skin treatment area), through the body of the user and back through the hand or palm-engaging electrode 32, to the treatment unit 14.

Figures 4, 5:
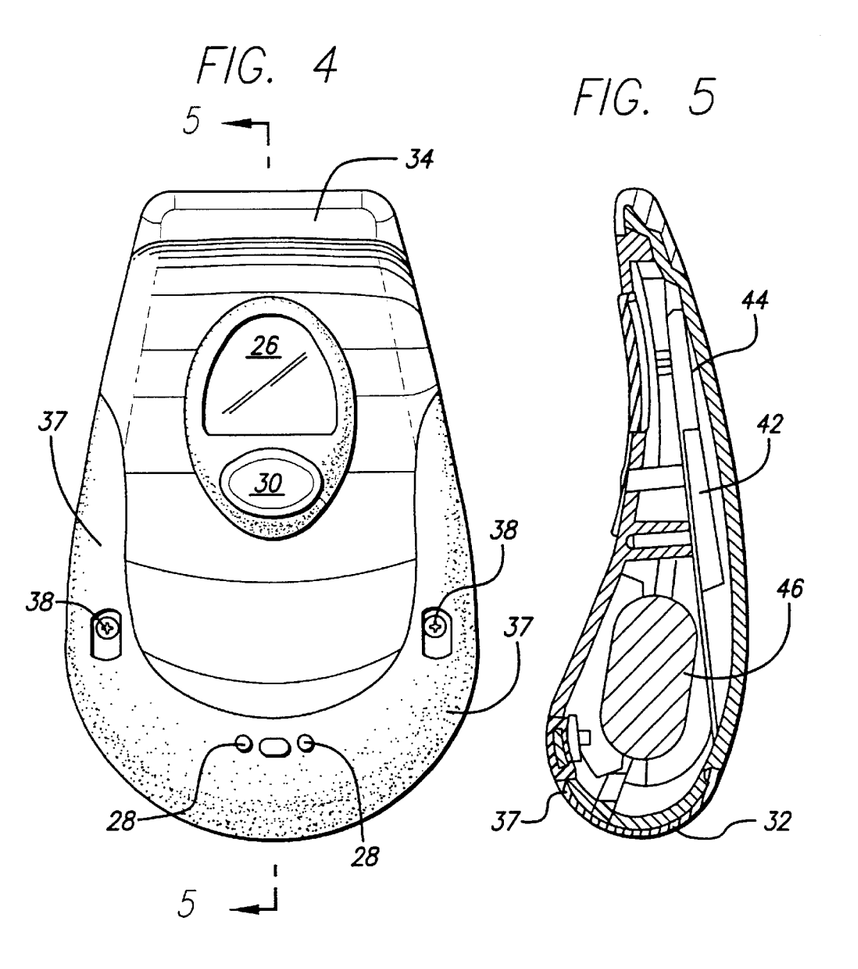
FIG. 4 is a top view of the skin treatment unit.
FIG. 5 is a cross-sectional view taken along lines 5—5 of FIG. 4.
Figure 6:
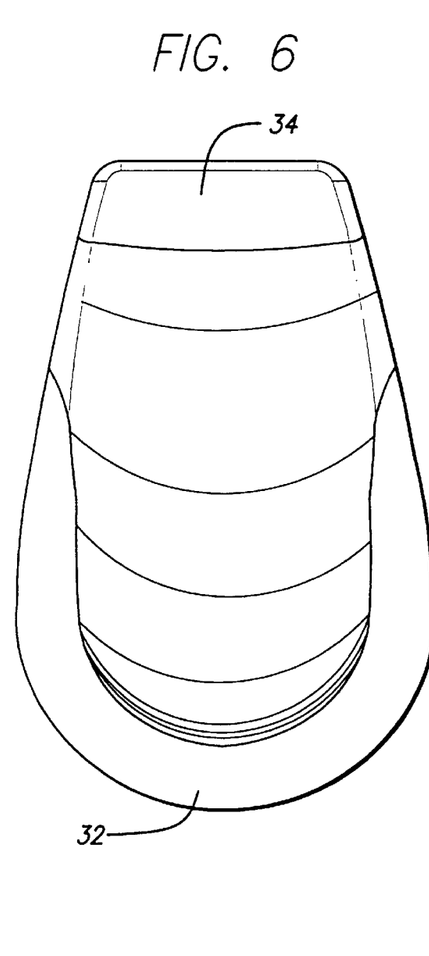
FIG. 6 is a rear view of the skin treatment unit.
Figure 7:
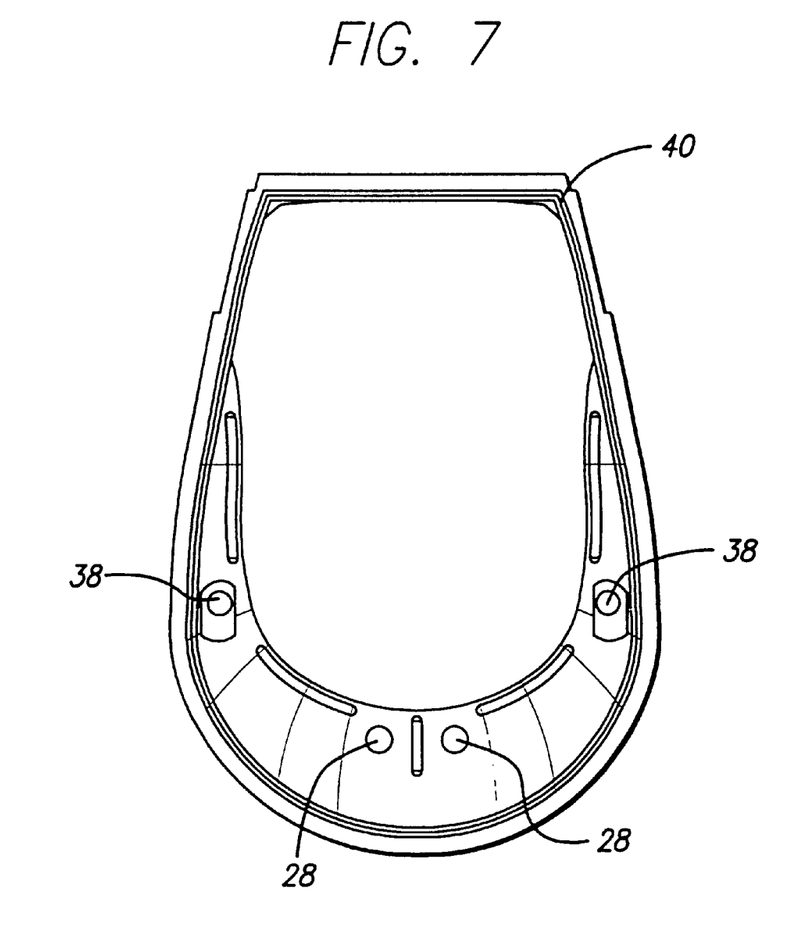
FIG. 7 is a view of one-half of the enclosing housing, showing the peripheral rubber seal making the housing watertight.

FIG. 4 illustrates a top view of the skin treatment unit 14. FIG. 5 shows a cross-sectional view taken along lines 5—5 of FIG. 4. FIG. 6 is a rear view of the treatment unit 14. FIG. 7 is a view of one-half of the enclosing housing. On the surface of the treatment unit 14, there is a rubber grip portion 37 provided to enable the user to have a better hold of the unit 14. Inside the treatment unit 14, there is a rechargeable battery 46 situated in the lower portion of the unit 14. As stated above, one feature of the unit 14 is the provision of a skin treatment unit 14 that is rechargeable. The battery unit 46 may be implemented by the use of two commercially available AA size NiCad batteries. These batteries may be permanently connected in series and shrink wrapped. As shown in FIGS. 5 and 7, the treatment unit 14 further includes a peripheral rubber seal 40 to make the unit's housing watertight. There is also a printed circuit board (PCB) 42 mounted within the treatment unit 14. The PCB 42 has a microprocessor 70 (see FIG. 8A) mounted thereon, for executing a software program to interface with an electronic circuitry to provide various functions or modes of operations. The microprocessor 70, the software program, the electronic circuitry, and the various modes of operations will be described in more details below.

Figure 8A:
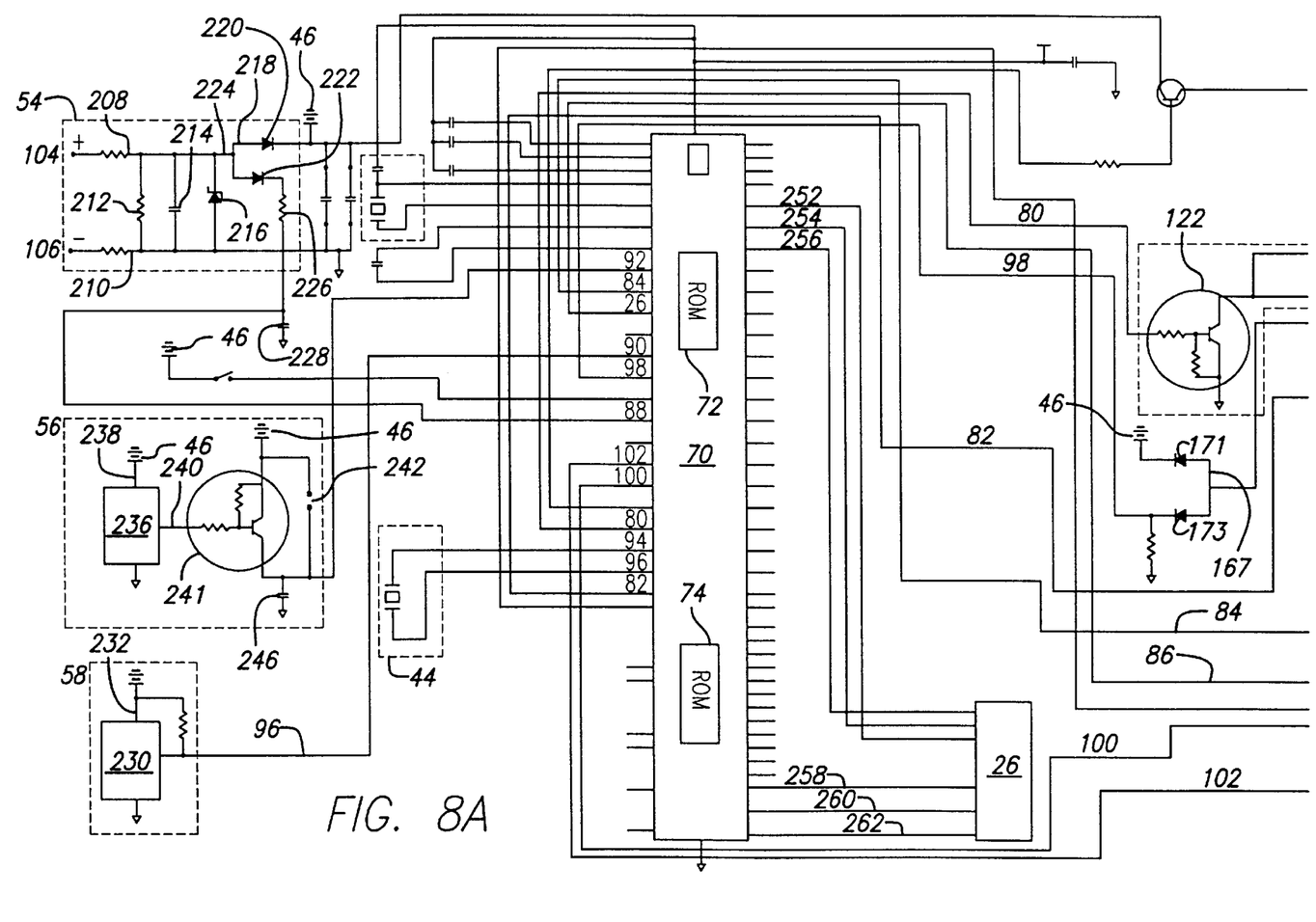
FIGS. 8A–8B show a circuit diagram with major sections of the circuitry enclosed in dash-dot blocks.
Figure 8B:
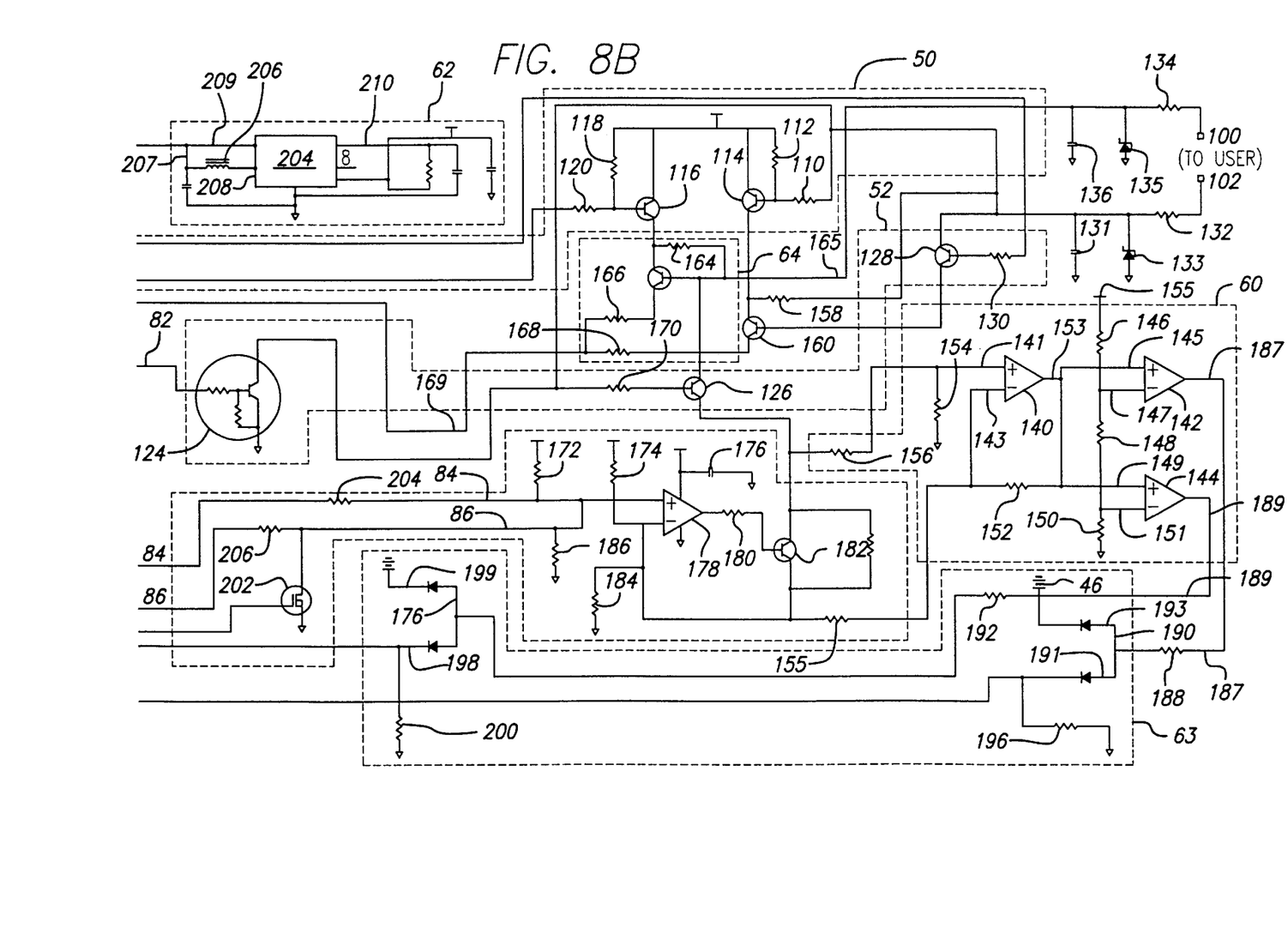

FIGS. 8A–8B show the electronic circuit diagram with major sections of the circuitry enclosed in dashed-dot blocks. The electronic circuit includes a microprocessor 70 fabricated on a single chip along with read-only memory (ROM) 72 and random-access memory (RAM) 94 associated therewith. In the preferred embodiment, a 4-bit microprocessor is used; however, any microprocessor providing similar functions may generally be used. The microprocessor 70 executes a software program stored in ROM 72 to interface with other hardware components in the circuitry to provide various functions or modes of operations. More details on the software program steps will be provided below.

The treatment unit 14 in accordance to the current invention provides two skin treatment modes, including CLEANSE MODE and MOISTURIZE MODE. The cleansing process is an anaphoresis process where a negative-to-positive current is used to induce an alkaline pH cleanser into the skin to open pores and deeply cleanse the skin. Prior to putting the treatment unit 14 in CLEANSE MODE, a user should first thoroughly clean a skin portion where the user wishes to apply the skin treatment, such as the user's face, and then apply a water-based, alkaline pH cleanser to the skin portion. A pH level is used in expressing both acidity and alkalinity on a scale whose values run from 0 to 14 with 7 representing neutrality, numbers less 7 representing increasing acidity, and numbers greater than 7 representing increasing alkalinity. The alkaline pH cleanser has a preferred pH level of approximately 8; however, the pH level of the cleanser may be in the general range from about 7 to about 9 or 10. After applying the cleanser to the skin portion, the user should then pick up the skin treatment unit 14 that is currently turned off or in OFF MODE, press the switch to put the unit 14 in CLEANSE MODE, and hold the unit 14 to the skin portion to be treated such that the skin treatment electrode 34 contacts the skin. As the user applies the treatment unit 14 to the skin portion, a negative-to-positive current is applied to the skin.

On the other hand, the moisturizing process is a cataphoresis process where a positive-to-negative current is used to induce an acid pH moisturizer into the skin to close pores and deeply moisturize the skin. The acid pH moisturizer has a preferred pH level of approximately 6; however, the pH level may generally be in the range of about 4 or 5 to about 7. Prior to using the skin treatment unit 14 in MOISTURIZE MODE, the user should have applied an acidic pH moisturizer to the skin portion to be treated. Then the user should put the treatment unit 14 in MOISTURIZE MODE, and apply the unit 14 to the skin portion such that the skin treatment electrode 34 contacts the skin. As the user applies the treatment unit 14 to the skin portion, a positive-to-negative current is applied to the skin.

To enable both a CLEANSE MODE and a MOISTURIZE MODE, the treatment unit's 14 electronic circuitry provides an output polarity switch function. Turning to FIG. 8B, dashed-dot blocks referred to with reference numerals 50 and 52 together show the sections of the circuitry which provide an output polarity switch functionality. Transistors 122 and 124 are controlled by the microprocessor 70 through conductors 80 and 82 respectively. When the treatment unit 14 is in operation, the microprocessor 70 only turns on either transistor 122 or transistor 124, but not both, at any single given time. The microprocessor 70 sends a logical signal through conductor 80 to turn on transistor 122, and through conductor 82 to turn on transistor 124.

On the other hand, when transistor 124 is turned on, transistor 125 is subsequently turned on by current flowing through resistor 170, and transistor 114 is also turned on by current flowing through resistor 110I. As a result, the current flows through resistor 134 to terminal 100 to deliver a negative-to-positive current to the user, thereby facilitating the deep cleansing of the skin. Zener diode 135 is used to protect against transient voltage by clamping down or stabilizing the voltage going into resistor 134.

When transistor 122 is turned on, transistor 116 is subsequently turned on by current flowing through resistor 120, and transistor 128 is also turned on by current flowing through resistor 130. As a result, the current flows through resistor 132 to terminal 102 to deliver a positive-to-negative current to the user, thereby facilitating the deep moisturizing of the skin. Zener diode 133 is used to protect against transient voltage by clamping down or stabilizing the voltage going into resistor 132.

Block 54 shows the portion of the circuitry that enables the recharging of the battery 46. Terminal 104 is positive, and terminal 106 is negative. Current flows from terminal 104 through resistor 208 into switching diode 218. Zener diode 216 maintains a constant voltage level at conductor 224. From conductor 224 current flows through the upper portion 220 of the switching diode 218 into the battery 46, and through the lower portion 222 of the switching diode 218 through resistor 226 and charges capacitor 228. The microprocessor 70 senses the charge level of capacitor 228 through line 88. Note that resistor 226 slows down the charge rate of capacitor 228 such that capacitor 228 reaches a charge level equivalent to a logical one at approximately the same time as the battery 46 becomes fully charged. Thus, by sensing the charge level of capacitor 228, the microprocessor 70 can determine whether the battery 46 is being charged or is fully charged. Since it can detect the charge status of the battery 46, the microprocessor 70 can in turn inform the user of the charge status by display either "CHARGING" or "DONE CHARGING" to the alphanumeric display 26.

Block 58 includes the low battery detection circuitry. Integrated circuit 230 is a voltage regulator with a voltage threshold. In the preferred embodiment, the integrated circuit 230 may be a voltage regulator with a 2.3 volts threshold, part number XC61AC2302M, manufactured by Torex. Conductor 232, which is coupled to the battery 46, provides the input to voltage regulator 230. The output of voltage regulator 230 goes to line 90 of the microprocessor 70. When the voltage of the battery 46 is above the voltage threshold of the voltage regulator 230, the output of voltage regulator 230 is a logical one, which signifies to the microprocessor 70 that the battery is not low. However, when the voltage of the battery 46 is below the voltage threshold of the voltage regulator 230, the output is a logical zero which signifies to the microprocessor 70 that the battery is low. When the microprocessor 70 knows that the battery 46 is low, it proceeds to take appropriate actions including informing the user by displaying a blinking legend "LOW BATTERY" on the alphanumeric display 26.

Block 56 includes the power reset circuitry. Integrated circuit 236 is a voltage regulator with a voltage threshold. In the preferred embodiment, the integrated circuit 236 may be a voltage regulator with a 2.1 volts threshold, part number XC61AC2102M, manufactured by Torex. Conductor 238, which is coupled to the battery 46, provides the input to voltage regulator 236. The output of voltage regulator 236 is connected to conductor 240 which is connected to the base of transistor 241. When the voltage of the battery 46 is below the voltage threshold of the voltage regulator 236, the output is a logical zero which turns on transistor 241. Once transistor 241 is turned on, current flows from the battery 46 through the emitter to the connector of transistor 241 into line 92 of the microprocessor to cause a system reset. A system reset could also be caused by closing or connecting jumper 242. When jumper 242 is closed or connected, current flows from the battery 46 through the connected jumper 242 into line 90 of the microprocessor. Line 90 is the RESET line of the microprocessor 70.

Block 64 includes the skin detection circuitry. When the user properly holds the skin treatment unit 14 to the skin portion to be treated, current flows from terminal 100 through conductor 165 into the base and out to the connector of transistor 162, then through resistor 166 into switching diode 167. At the switching diode 167, current flows through the upper portion 171 into the positive terminal of the battery 46, and through the lower portion 173 to supply sufficient voltage to indicate a logical one on line 98 to the microprocessor 70, indicating that there is sufficient contact between the treatment unit 14 and the skin of the user.

Block 62 includes a step-up transformer circuitry to raise the voltage level of the system. Current flows through conductor 207, inductor 206 into pin 208 of the voltage regulator 204 to supply an unregulated voltage to the regulator 204. The voltage regulator 204 also receives a DC input through conductor 209. The voltage regulator 204 in turn produces a stepped-up, stable, and constant DC output. In the preferred embodiment, the integrated circuit 204 may be a 12.8 volts voltage regulator/DC-to-DC converter, part number TK11816MTL, manufactured by Toko America, Inc.

Blocks 60 and 63 together provide a mechanism to sense moisture or resistance on the skin and to feed the result back to the microprocessor 70. The main principle adopted is that a lower level of moisture or a higher level of resistance would result in a higher voltage level in the system. Therefore, the skin moisture or resistance circuitry included in block 60 essentially measures the voltage level at key points in the system to determine the level of skin moisture or resistance. Operational amplifier (op-amp) 140 serves as a differential amplifier having a noninverting input 141 and an inverting input 143. It should be noted that resistors 152, 154, 155, and 156 have substantially the same resistive values. Thus, the feedback ratio into op-amp/differential amplifier 140 is approximately 1. Note that the voltage coming into the noninverting input 141 of op-amp 140 comes from the connector of transistor 182, and the inverting input 143 into op-amp 140 is essentially equal to the voltage across resistor 155. Op-amps 142 and 144 serves as comparators used to compare the output 153 of op-amp/differential amplifier 140 to different known voltage levels. The output 153 of op-amp 140 becomes the input voltage of op-amp/comparator 142 and also op-amp/comparator 144. The reference voltages 147 and 151 of op-amp/comparators 142 and 144 respective are supplied from source 155. Note that the voltage from source 155 is dropped across resistor 146 prior to reaching op-amp/comparator 142, and is again dropped across resistor 148 prior to reaching op-amp/comparator 142. The output 187 of op-amp/comparator 142 flows through resistor 192 and lower portion 199 of switching diode 198 into line 100 of the microprocessor 70. The output 189 of op-amp/comparator 144 flows through resistor 188 and lower portion 191 of switching diode 190 into line 102 of the microprocessor 70. From the values supplied through lines 100 and 102, the microprocessor may determine the level of skin moisture or resistance.

Once supplied with information about the skin moisture or resistance, the microprocessor 70 may appropriately adjust the current level to maintain a constant output of power ($P=I^2R$), thereby avoid shocking users whose skins has a higher level of moisture or resistance. The microprocessor 70 adjusts the current level by sending out appropriate logic signals on lines 84 and 86.

Other components of the electronic circuitry include a buzzer 44 and an LCD 26. In the preferred embodiment, the buzzer 44 may be a 20 millimeter buzzer, part number PAR001-002, manufactured by Yat Tsun. The buzzer 44 is activated by lines 94 and 96 of the microprocessor. Note that lines 94 and 96 are inversions of one another. In the preferred embodiment, the LCD 26 may be a 3-planes, reflective LCD, manufactured by Truly Semiconductor. The LCD 26 is controlled by the microprocessor 70 through lines 252, 254, 256, 258, 260, and 262.

Figure 9A:
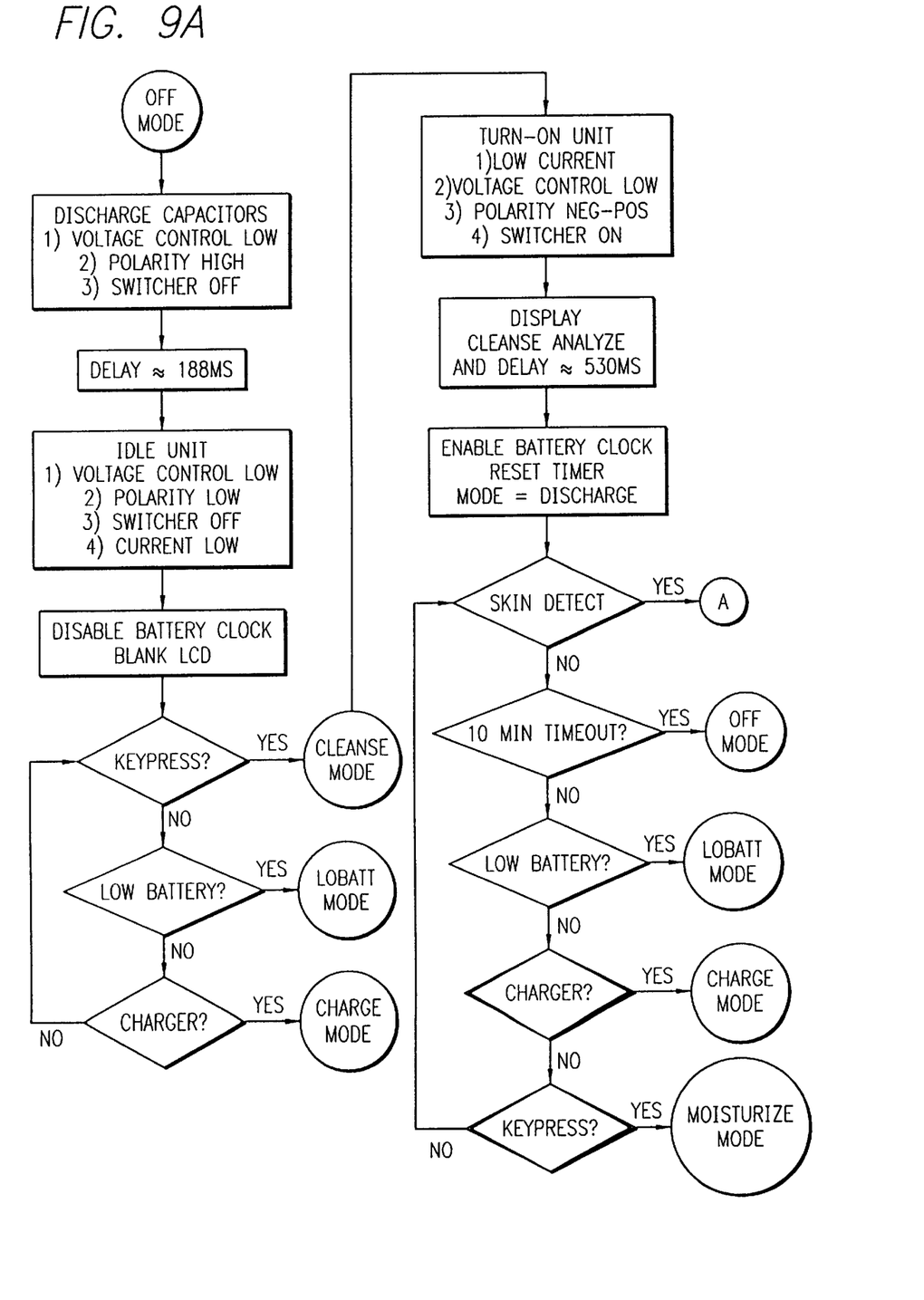
FIGS. 9A–9C show a block logic diagram showing the microprocessor program steps involved in implementing the CLEANSE MODE forming one part of a skin treatment regimen.
Figure 9B:
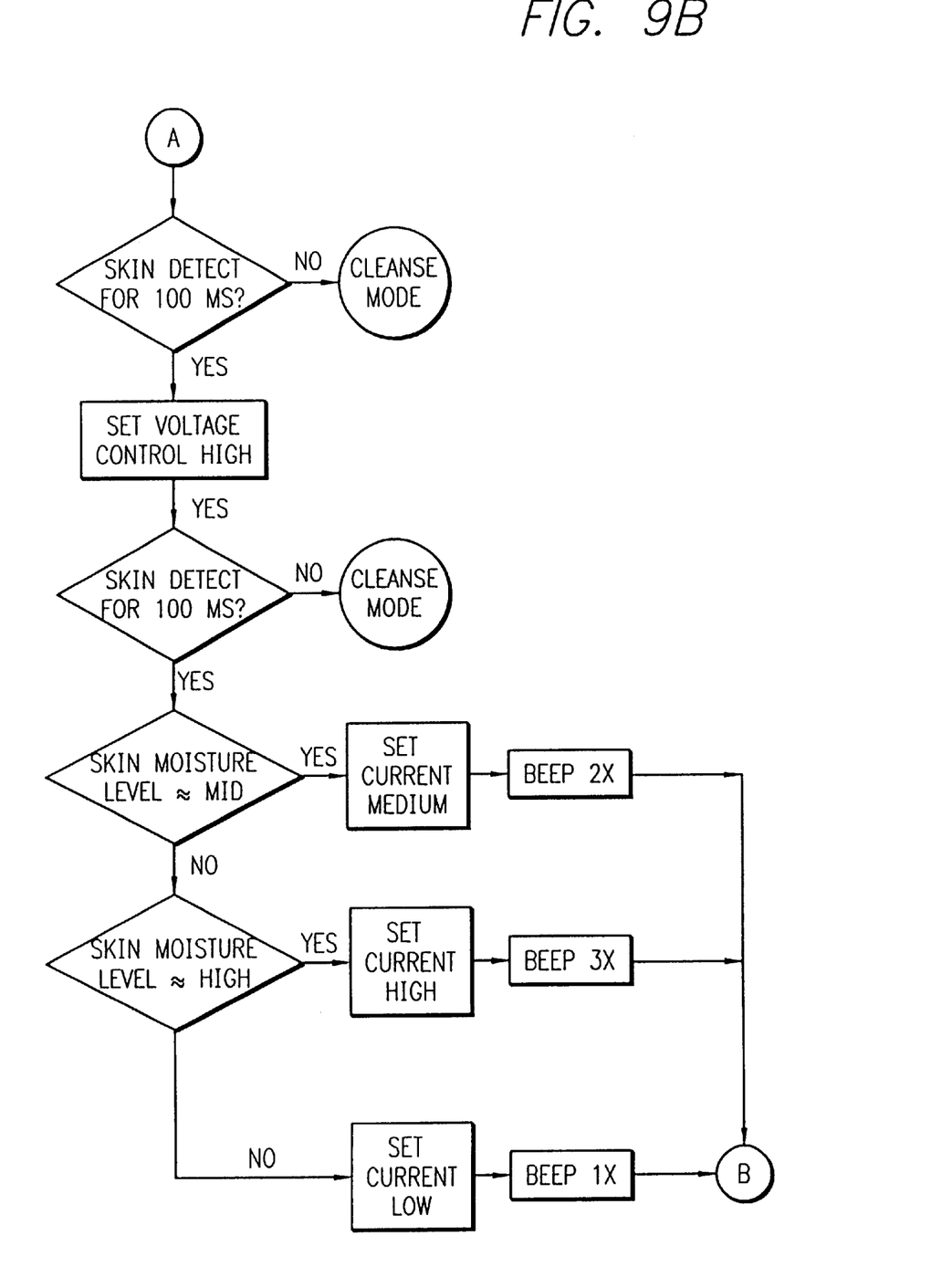
Figure 9C:
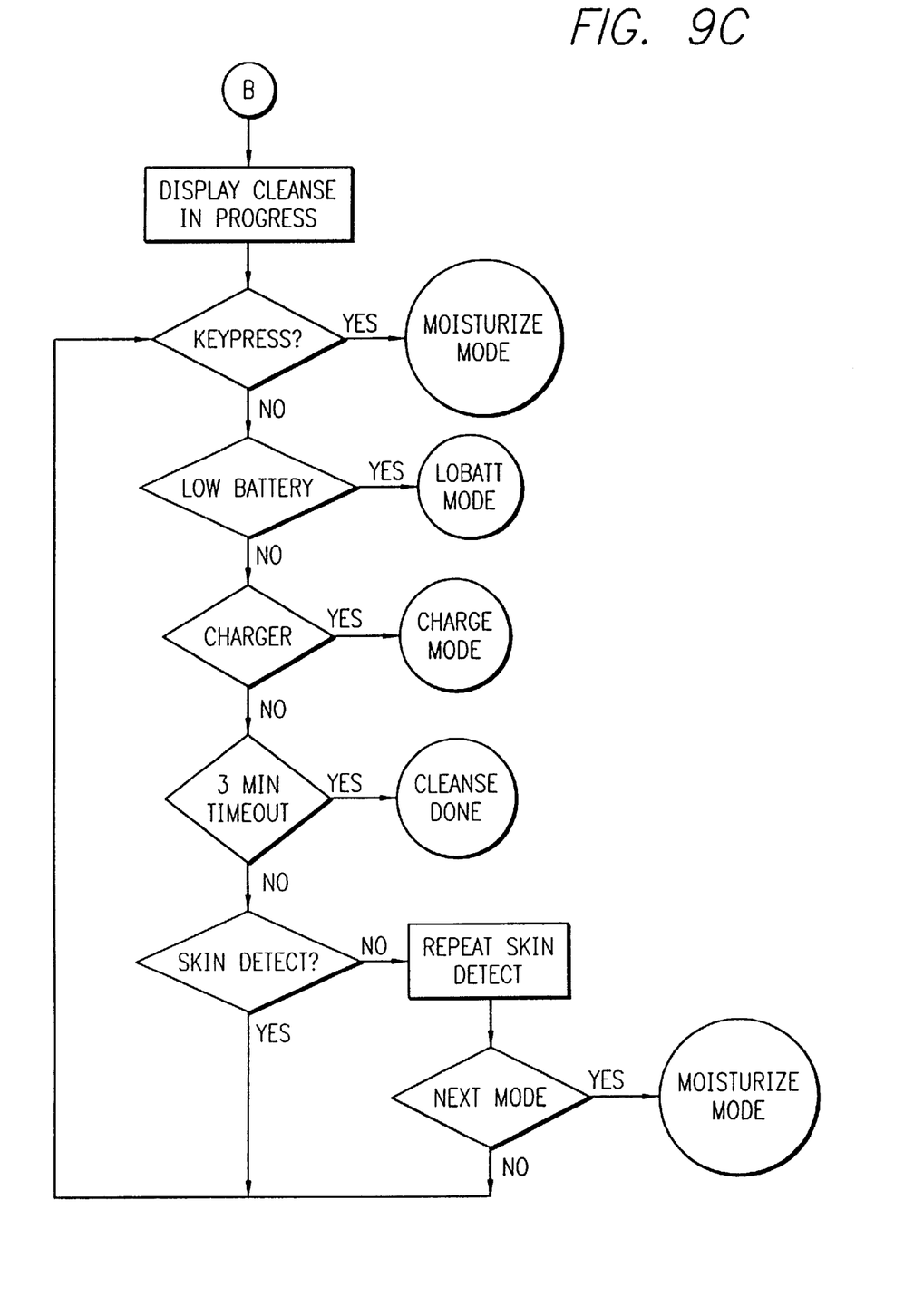

As stated above, the exemplary skin treatment unit 14 provides two skin treatment modes, including CLEANSE MODE and a MOISTURIZE MODE. FIGS. 9A–9C shows block logic diagrams of the steps of the software program in implementing the CLEANSE MODE of the skin treatment regimen. Prior to putting the treatment unit 14 in CLEANSE MODE, a user should first thoroughly clean a skin portion where the user wishes to apply the skin treatment, and then apply a water-based, alkaline pH cleanser to the skin portion. After applying the cleanser to the skin portion, the user should then pick up the skin treatment unit 14 that is currently turned off or in OFF MODE, press the switch 30, and hold the unit 14 to the skin portion to be treated such that the skin treatment electrode 34 contacts the skin.

As seen in FIG. 9A, the pressing of the switch takes the treatment unit 14 from the OFF MODE to the CLEANSE MODE. Upon entering CLEANSE MODE, the microprocessor 70 of the unit 14 turns on the skin treatment unit 14, sets the current flow and the voltage control to low, changes the polarity from negative to positive, and tells the hardware to step up the voltage. Then the skin treatment unit 14 displays the legend "CLEANSE ANALYZE" on the alphanumeric display 26, resets a timer which is used to monitor a time out interval and a application duration, and proceeds to detect the level of skin moisture.

However, if the user fails to properly hold the treatment unit 14 to the skin portion, the unit 14 will turn itself off after a predetermined time out period. The preferred predetermined time out interval is approximately ten minutes; however, the interval may generally be in the range of about five to fifteen minutes. The purpose of having an automatic time out is to conserve power when the treatment unit 14 is not in use to keep the user from having to recharge the battery 46 too frequently.

During the predetermined time-out period, the skin treatment unit 14 continuously monitors whether the user properly holds the unit 14 to the skin portion to be treated, whether the battery 46 is low, whether the recharger assembly 18, 20, 22 is attached, and whether the switch is pressed. If the battery 46 is low, the skin treatment unit 14 automatically enters LOBATT MODE (see FIG. 12). If the battery 46 is not low but the recharger assembly 18, 20, 22 is attached, the skin treatment unit 14 is put in CHARGE MODE (see FIG. 12). If the battery 46 is not low, the recharger assembly 18, 20, 22 is not attached, and the switch is pressed, the skin treatment unit 14 is instead put in MOISTURIZE MODE.

If the user properly holds the skin treatment unit 14 to the skin portion to be treated, the unit 14 automatically selects one of a plurality of current levels depending upon the level of skin moisture detected (see FIG. 9B). In the preferred embodiment, there are three current levels, including LOW, MEDIUM, or HIGH. The preferred LOW current level is approximately 0.25 mA (milliamp or a thousandth of an amp); the preferred MEDIUM current level is approximately 0.375 mA; and the preferred HIGH current level is approximately 0.5 mA. However, these current levels may be continuously varied and may generally be in the range of about 0.1 mA to 0.6 mA. Furthermore, the MEDIUM current level is used as the preferred default current level. After the current level is selected, the buzzer 44 is sounded once for LOW, twice for MID, and thrice for HIGH.

Turning now to FIG. 9C, the legend "CLEANSE IN PROGRESS" is displayed on the LCD after the buzzer 44 has been sounded. At this point, the user should then apply the skin treatment unit 14 to the skin portion to be treated by moving the unit 14 over all areas of the skin portion for a predetermined application duration. The preferred predetermined application duration is approximately three minutes; however, the application duration may be in the general range of about one to six minutes. During the predetermined application duration, the treatment unit 14 continuously monitors whether the switch 30 is pressed, whether the battery 46 is low, whether the recharger assembly 18, 20, 22 is attached to the unit 14, and whether the application duration has expired. If the switch is pressed, the treatment unit 14 enters MOISTURIZE MODE. If the switch is not pressed and the battery 46 is low, the unit 14 enters LOBATT MODE (see FIG. 12). If the switch is not pressed, the battery 46 is not low, and the recharger assembly 18, 20, 22 is attached, the unit 14 enters CHARGE MODE (see FIG. 12).

Figures 10, 11:
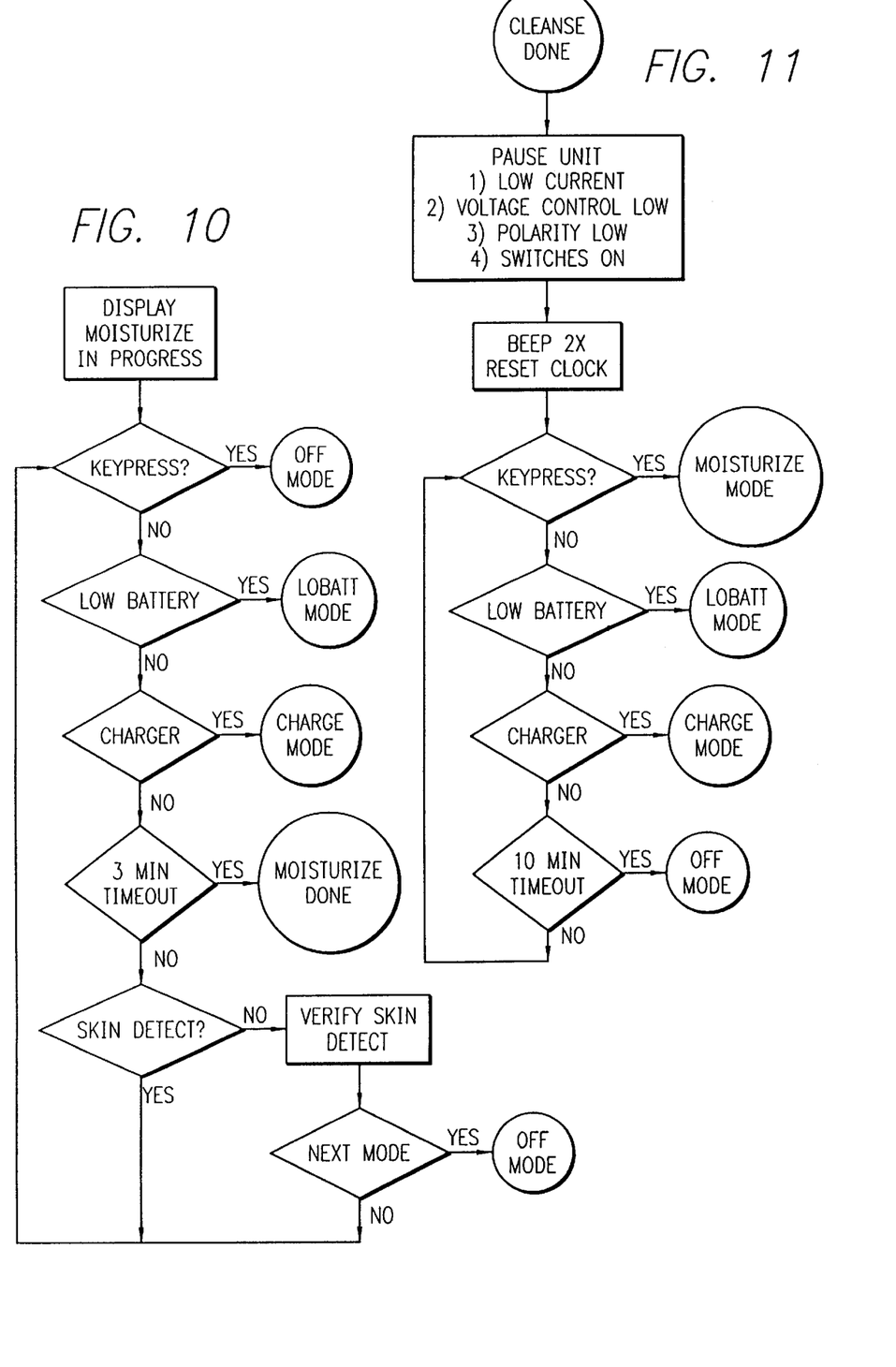
FIG. 10 is a block logic diagram relating to the MOISTURIZE MODE.
FIG. 11 is a block program diagram indicating routine steps accomplished following completion of the cleanse step of the skin treatment program.

When the predetermined application duration expires, the treatment unit 14 enters CLEANSE DONE MODE. FIG. 11 shows the programming steps executed in CLEANSE DONE MODE. In CLEANSE DONE MODE, the skin treatment unit 14 first goes into a PAUSE state where the current flow, the voltage control and the polarity are all set to low. The unit 14 then sounds the buzzer 44 twice to notify the user that the application duration has expired, and resets a clock which is used to keep track of the time out interval and the application duration. While in CLEANSE DONE MODE, the skin treatment unit 14 enters OFF MODE to shut itself off if the user fails to press the switch 30 within the predetermined time out interval. Also during the predetermined time out interval, the skin treatment unit 14 continuously monitors whether the switch 30 is pressed, whether the battery 46 is low, whether the recharger assembly 18, 20, 22 is attached, and whether the predetermined time out interval has expired. If the switch 30 is not pressed and the battery 46 is low, the skin treatment unit 14 enters LOBATT MODE (see FIG. 12). If the switch 30 is not pressed, the battery 46 is not low, and the recharger assembly 18, 20, 22 is attached, the skin treatment unit 14 enters CHARGE MODE (see FIG. 12). If the switch 30 is pressed, the skin treatment unit 14 is put in MOISTURIZE MODE.

As noted above, the moisturizing process is a cataphoresis process where an acid pH moisturizer is induced into the skin to close pores and deeply moisturize the skin. Prior to using the skin treatment unit 14 in MOISTURIZE MODE, the user should have applied an acidic pH moisturizer to the skin portion to be treated. Then the user should put the treatment unit 14 in MOISTURIZE MODE, and apply the unit 14 to the skin portion such that the skin treatment electrode 34 contacts the skin.

When the treatment unit 14 is put in MOISTURIZE MODE, the unit's 14 microprocessor 70 turns on the unit 14, sets the current flow and the voltage control to low, and changes the polarity from positive to negative. Furthermore, the skin treatment unit 14 displays the legend "MOISTURIZE ANALYZE" on the alphanumeric display 26, resets the timer which is used to keep track of the time out interval and the application duration, and proceeds to detect the level of skin moisture.

However, if the user fails to properly hold the treatment unit 14 to the skin portion to be treated, the unit 14 turns itself off after the predetermined time out interval. During the predetermined time out interval, the skin treatment unit 14 continuously monitors whether the unit 14 is held to the skin portion to be treated, whether the battery 46 is low, whether the recharger assembly 18, 20, 22 is attached, and whether the switch 30 is pressed. If the battery 46 is low, the unit 14 automatically enters LOBATT MODE (see FIG. 12). If the battery 46 is not low and the recharger assembly 18, 20, 22 is attached, the skin treatment unit 14 puts itself in CHARGE MODE (see FIG. 12). If the battery 46 is not low, the recharger assembly 18, 20, 22 is not attached, and the switch 30 is pressed, the skin treatment unit 14 goes into OFF MODE when the predetermined time out interval expires.

If the user properly holds the skin treatment unit 14 to the skin portion to be treated, the unit 14 automatically selects one of a plurality of current levels depending upon the level of skin moisture and resistance detected. As noted above, the preferred embodiment has three current levels, including LOW, MEDIUM, or HIGH. Furthermore, the MEDIUM current level is used as the preferred default current level. After the current level is selected, the buzzer 44 is sounded once for LOW, twice for MID, and thrice for HIGH.

Turning now to FIG. 10, the treatment unit 14 displays the legend "MOISTURIZE IN PROGRESS" on the alphanumeric display 26 after the buzzer 44 is sounded. At this time, the user should then apply the skin treatment unit 14 to the skin portion to be treated by moving the unit over all areas of the skin portion for a predetermined application duration. During the predetermined application duration, the treatment unit continuously monitors whether switch 30 is pressed, whether the battery 46 is low, whether the recharger assembly 18, 20, 22 is attached to the unit 14, and whether the application duration has expired. If the switch is pressed, the treatment unit 14 enters OFF MODE. If the battery 46 is low, the skin treatment unit 14 enters LOBATT MODE (see FIG. 12). If the battery 46 is not low and the recharger assembly 18, 20, 22 is attached, the treatment unit 14 enters CHARGE MODE (see FIG. 12).

When the predetermined application duration expires, the skin treatment unit 14 enters MOISTURIZE DONE mode. Upon entering the MOISTURIZE DONE MODE, the skin treatment unit 14 first enters a PAUSE state where the current flow, the voltage control, and the polarity are all set to low. Then the buzzer 44 is sounded twice to notify the user that the application duration has expired, and the timer is reset.

While in MOISTURIZE DONE MODE, the skin treatment unit 14 enters OFF MODE to shuts itself off if the user fails to press the switch 30 within the predetermined time out interval. During the predetermined time out interval, the skin treatment unit 14 continuously monitors whether the battery 46 is low, whether the recharger assembly 18, 20, 22 is attached, and whether the switch is pressed. If the battery 46 is low, the skin treatment unit 14 automatically enters LOBATT MODE (see FIG. 12). If the battery 46 is not low but the recharger assembly 18, 20, 22 is attached, the skin treatment unit 14 automatically enters CHARGE MODE (see FIG. 12). If the battery 46 is not low, the recharger assembly 18, 20, 22 is not attached, and the switch is pressed, the skin treatment unit 14 enters OFF MODE.

As seen in FIG. 9A, all capacitors in the electronic circuitry of the skin treatment unit 14 are discharged when the unit 14 is put in OFF MODE. Then the voltage control is set to low, the polarity is set to high, and the voltage is stepped down. Following a delay of approximately 188 MS (milli-second or a thousandth of a second), the treatment unit 14 is put in an IDLE state where the voltage control, the polarity, and the current level are set to low. The battery clock is then disabled, and the alphanumeric display 26 is blanked. Even in OFF MODE, the unit 14 still continuously monitors whether the switch 30 is pressed, whether the battery 46 is low, and whether the recharger assembly 18, 20, 22 is attached. If the switch 30 is pressed, the unit 14 goes from OFF MODE to CLEANSE MODE. If the switch 30 is not pressed and the battery 46 is low, the unit 14 enters LOBATT MODE. If the switch 30 is not pressed, the battery 46 is not low, and the recharger assembly 18, 20, 22 is attached, the unit 14 enters CHARGE MODE.

Figure 12:
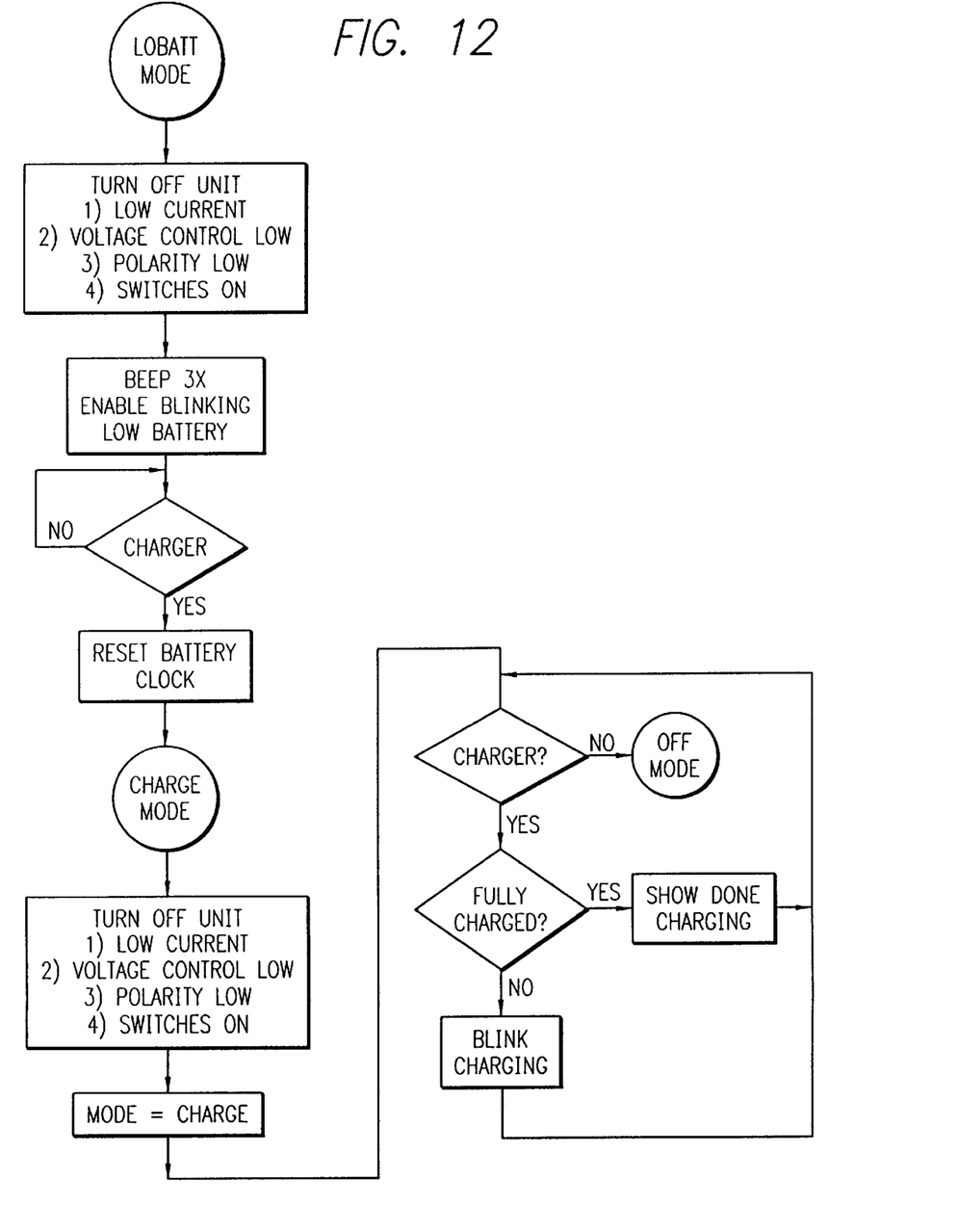
FIG. 12 is a block program diagram indicating the steps involved in recharging the skin treatment unit.

FIG. 12 illustrates the program steps of implementing the LOBATT MODE and the CHARGE MODE. Upon entering LOBATT MODE, the treatment unit 14 is turned off; and the current level, the voltage control, and the polarity are set to low. A blinking legend "LOW BATTERY" will appear on the alphanumeric display 26. Then the treatment unit 14 monitors whether the recharger assembly 18, 20, 22 is attached.

If the recharger assembly 18, 20, 22 is attached, the treatment unit 14 enters CHARGE MODE. Upon entering CHARGE MODE, the treatment unit 14 is turned off; and the current level, the voltage control, and the polarity are set to low. At this point, if the treatment unit 14 detects that the recharger assembly 18, 20, 22 is no longer attached, the unit 14 goes into OFF MODE. If the recharger assembly 18, 20, 22 is properly attached, the unit's battery 46 is charged until it is full. While the battery 46 is being charged, the treatment unit displays a blinking legend "CHARGING". When the battery 46 is fully charged, the treatment unit 14 displays a blinking legend "DONE CHARGING".

A summarized description of the skin treatment procedure steps is provided in Table I, which is included below.

TABLE I

| UNIT POSITIONED IN CHARGER CLIP | Done Charging | Low Battery | CHARGING |
|---|---|---|---|
| | | | 1. LOW BATTERY COMES ON & BLINKS & THE UNIT BEEPS THREE TIMES WHEN BATTERY LEVEL REACHES 10%, & THEN GOES OFF WHEN CHARGING IS INITIATED |
| | | | 2. CHARGING BLINKS UNTIL COMPLETE |
| | | | 3. DONE CHARGING COMES ON & STAYS ON UNTIL UNIT IS REMOVED FROM THE CHARGING BASE OR THE AC ADAPTER IS UNPLUGGED |
| | | | 3. UNIT CAN BE CHARGED ANYTIME |
| | | | 4. IF UNIT IS PLACED IN CHARGING POSITION WHILE STILL ON, IT WILL AUTOMATICALLY SWITCH TO CHARGING MODE |

TABLE I-continued

TABLE I-continued

| OFF |
| --- |
| IF UNIT IS NOT MANUALLY TURNED OFF, IT WILL AUTOMATICALLY TURN OFF AFTER TEN MINUTES. IF UNIT IS NOT USED FOR A LONG PERIOD OF TIME AND THE BATTERY IS COMPLETELY DISCHARGED, IT WILL BE NECESSARY TO PLACE THE UNIT IN THE CHARGING CLIP AND CHARGE FOR 16+ HOURS. NOTHING WILL SHOW IN THE LCD WINDOW UNTIL THE BATTERY HAS CHARGED TO THE MINIMUM THRESHOLD LEVEL. AT THAT TIME THE UNIT WILL BEEP THREE TIMES, AND WILL DISPLAY INFORMATION IN THE CHARGING MODE AND COMPLETE THE NORMAL CHARGING CYCLE. |

Although the present invention has been described in terms of the preferred embodiment above, numerous modifications and/or additions to the above-described preferred embodiments would be readily apparent to one skilled in the art. Thus, by way of example and not of limitation, the acid pH moisturizer has a preferred pH level of approximately 6; however, the pH level may generally in the range of about 4 or 5 to about 7. As another example, the alkaline pH cleanser has a preferred pH level of approximately 8 pH; however, the pH level of the cleanser may be in the general range of about 7 to about 9 or 10. Also, the predetermined time out interval is preferably about ten minutes; however, the interval may generally be in the range of approximately five to fifteen minutes. Furthermore, the predetermined application duration is preferably about three minutes; however, the duration may generally be in the range of approximately one to six minutes. In addition, the preferred LOW current level is approximately 0.25 mA (milliamp or a thousandth of an amp); the preferred MEDIUM current level is approximately 0.375 mA; and the preferred HIGH current level is approximately 0.5 mA. However, these current levels may be continuously varied and may generally be in the range of about 0.1 mA to 0.6 mA. Accordingly, the present invention is not to be limited to the particular mechanical, electrical, or program steps or embodiments as shown the drawings and described in detail hereinabove.

What is claimed is:

1. A system for electrically treating the skin comprising:
a handheld electrical skin treatment unit including a housing having an internal chamber containing electrical circuitry including a microprocessor and a rechargeable battery, an alphanumeric display coupled to said microprocessor, and first and second external electrically conductive electrodes connected to said circuitry, said first conductive electrode being a palm electrode adapted to be in continuous contact with the user's hand, and said second skin electrode being adapted to apply electrical current to the skin of the user to be treated; said unit also including exposed recharging terminals for recharging said battery;
said microprocessor having a read only memory associated therewith, and said microprocessor executing a software program stored in said read only memory to provide skin treatment procedure steps;
said alphanumeric display being coupled to said microprocessor to indicate the procedure step under way with said unit during successive program steps;
a recharger assembly including a low voltage power supply and a recharging mount for holding said unit with said exposed recharging terminals engaging corresponding terminals in said recharging mount with said alphanumeric display exposed; and
a stand for said unit for mounting said unit in a convenient location when it is not in use, but is in the charged state.

2. A handholdable electrical skin treatment unit as defined in claim 1 further including circuitry for displaying the charge status of said rechargeable battery.

3. A system as defined in claim 1 wherein said unit displays a legend indicating charge status while mounted in said recharging mount.

4. A system as defined in claim 1 wherein said read only memory includes successive states involving a first cleansing state wherein a cleansing legend is displayed and current of one polarity is supplied through said electrodes, and a second moisturizing state wherein a moisturizing legend is displayed and wherein current of the opposite polarity is supplied through said electrodes.

5. A system as defined in claim 1 wherein said microprocessor executes said software program to select a current level to be applied to the skin depending on the resistance encountered when said second electrode is applied to the skin.

6. A system as defined in claim 1 wherein said microprocessor executes said software program to apply electrical current to the skin for a predetermined application duration and thereafter automatically stops current flow.

7. A system as defined in claim 5 wherein said predetermined application duration is generally in the range of about one to six minutes.

8. A system as defined in claim 1 wherein said microprocessor executes a software program stored in said read only memory to turn off said treatment unit after a predetermined time out interval to conserve said rechargeable battery.

9. A system as defined in claim 8 wherein said predetermined time out interval is in the range of about five to fifteen minutes.

10. A system for electrically treating the skin comprising:
a handheld electrical skin treatment unit including a housing having an internal chamber containing electrical circuitry including a microprocessor and a rechargeable battery, an alphanumeric display coupled to said microprocessor, and first and second external electrically conductive electrodes connected to said circuitry, said first conductive electrode being a palm electrode adapted to be in continuous contact with the user's hand, and said second skin electrode being adapted to apply electrical current to the skin of the user to be treated; said unit also including exposed recharging terminals for recharging said battery;
said microprocessor having a read only memory associated therewith, and said microprocessor executing a software program stored in said read only memory to provide skin treatment procedure steps; and
said alphanumeric display being coupled to said microprocessor to indicate the procedure step under way with said unit during successive program steps.

11. A system as defined in claim 10 wherein the handheld electrical skin treatment unit further including circuitry for displaying the charge status of said rechargeable battery.

12. A system as defined in claim 10 wherein said read only memory includes successive states involving a first cleansing state wherein a cleansing legend is displayed and current of one polarity is supplied through said electrodes, and a second moisturizing state wherein a moisturizing legend is displayed and wherein current of the opposite polarity is supplied through said electrodes.

13. A system as defined in claim 10 wherein said microprocessor executes said software program to select a level of current to be applied to the skin depending on the resistance encountered when said second electrode is applied to the skin.

14. A system as defined in claim 10 wherein said microprocessor executes said software program to apply electrical current to the skin for a predetermined application duration, and thereafter automatically stops current flow.

15. A system as defined in claim 10 wherein said microprocessor executes said software program to turn off said treatment unit after a predetermined time out interval to conserve said rechargeable battery.

16. A method for cleansing and moisturizing the skin using a handheld electrical application unit having two electrodes, a first electrode for engagement with the hand, and a second electrode for engagement with the skin to be treated, the method comprising the steps of:

(a) applying a water based alkaline pH cleanser to the skin to be treated;

(b) cleansing the skin by applying a negative-to-positive current flow to the skin by engaging the second electrode to the skin and moving the second electrode over the skin, while engaging the first electrode with the hand of the user;

(c) removing the cleanser;

(d) applying an acidic moisturizer to the skin;

(e) reversing the current flow of the unit;

(f) moisturizing the skin by applying a positive-to-negative current flow to the skin by engaging the second electrode to the skin and moving the second electrode over the area of the skin to be treated while engaging the first electrode with the hand; and (g) initially testing the skin electrical properties, and automatically setting the current level of the unit in accordance with the measured electrical property.

17. A method for cleansing and moisturizing the skin using a handheld electrical application unit having two electrodes, a first electrode for engagement with the hand, and a second electrode for engagement with the skin to be treated, the method comprising the steps of:

(a) applying a water based alkaline pH cleanser to the skin to be treated;

(b) cleansing the skin by applying a negative-to-positive current flow to the skin by engaging the second electrode to the skin and moving the second electrode over the skin, while engaging the first electrode with the hand of the user;

(c) removing the cleanser;

(d) applying an acidic moisturizer to the skin;

(e) reversing the current flow of the unit;

(f) moisturizing the skin by applying a positive-to-negative current flow to the skin by engaging the second electrode to the skin and moving the second electrode over the area of the skin to be treated while engaging the first electrode with the hand; and (g) displaying a cleansing legend on an alphanumeric display of said electrical application unit while cleansing the skin, and displaying a moisturizing legend on said alphanumeric display while moisturizing the skin.

\* \* \* \* \*